US006013804A

United States Patent [19]

Kleefeld et al.

[11] Patent Number: 6,013,804

[45] Date of Patent: Jan. 11, 2000

[54] 1,3,4-OXADIAZOLIN-2-ONES AND THEIR USE AS PESTICIDES

[75] Inventors: Gerd Kleefeld, Neuss; Ulrike Wachendorff-Neumann, Neuwied, both of Germany

[73] Assignee: Bayer Aktiengesellschaft, Leverkusen, Germany

[21] Appl. No.: 09/029,106

[22] PCT Filed: Aug. 19, 1996

[86] PCT No.: PCT/EP96/03640

§ 371 Date: Feb. 20, 1998

§ 102(e) Date: Feb. 20, 1998

[87] PCT Pub. No.: WO97/08158

PCT Pub. Date: Mar. 6, 1997

[30] Foreign Application Priority Data

Aug. 30, 1995 [DE] Germany ........................... 195 31 892

[51] Int. Cl.$^7$ ....................... C07D 271/13; A01N 43/824

[52] U.S. Cl. ............................................ 548/144; 514/364

[58] Field of Search ............................. 548/144; 514/364

[56] References Cited

U.S. PATENT DOCUMENTS

| | | | |
|---|---|---|---|
| 4,246,403 | 1/1981 | Prossel et al. | 548/144 |
| 4,259,104 | 3/1981 | Edwards | 548/144 X |
| 4,943,583 | 7/1990 | Luthy, I | 514/364 |
| 5,418,246 | 5/1995 | Bettarini et al. | 514/364 |

FOREIGN PATENT DOCUMENTS

| | | | |
|---|---|---|---|
| 0270061 | 6/1988 | European Pat. Off. | 548/144 |
| 3631511 | 3/1988 | Germany . | |

*Primary Examiner*—Floyd D. Higel
*Attorney, Agent, or Firm*—Sprung Kramer Schaefer & Briscoe

[57] ABSTRACT

The present invention relates to 1,3,4-oxadiazolin-2-ones of the formula (I)

(I)

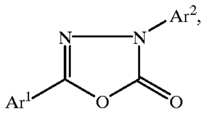

in which $Ar^1$ represents optionally substituted phenyl and $Ar^2$ represents optionally substituted biphenyl, to processes for their preparation and to their use for controlling animal pests.

9 Claims, No Drawings

1,3,4-OXADIAZOLIN-2-ONES AND THEIR USE AS PESTICIDES

This application is a 371 of PCT/EP96/03640 filed Aug. 19, 1996.

The present invention relates to novel 1,3,4-oxadiazolin-2-ones, to processes for their preparation and to their use for controlling animal pests.

It is already known that certain substituted 1,3,4-oxa(thia)diazolin-2-ones have insecticidal and acaricidal properties (cf. EP-A 0 270 061). However, the efficacy and/or duration of action of these prior art compounds, in particular at low application rates and concentrations, is not entirely satisfactory in all areas of use.

This invention, accordingly, provides novel 1,3,4-oxadiazolin-2-ones of the formula (I)

(I)

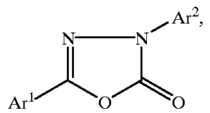

in which $Ar^1$ represents optionally substituted phenyl and $Ar^1$ represents optionally substituted biphenyl.

Furthermore, it has been found that 1,3,4-oxadiazolin-2-ones of the formula (I) are obtained when a) hydrazides of the formula (II)

(II)

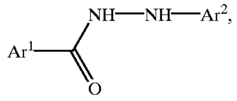

in which $Ar^1$ and $Ar^2$ are each as defined above are reacted with an acylating agent in the presence of a diluent and, if appropriate, in the presence of a base, or b) 3-phenyl-1,3,4-oxadiazolin-2-ones of the formula (III)

(III)

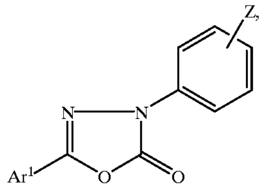

in which $Ar^1$ is as defined above and

Z represents a leaving group are reacted with boronic acids of the formula (IV)

$$R—B(OH)_2 \quad (IV),$$

in which

R represents optionally substituted phenyl in the presence of a base, if appropriate in the presence of a catalyst and in the presence of a diluent.

Furthermore, it has been found that the novel 1,3,4-oxadiazolin-2-ones of the formula (I) are highly suitable for controlling animal pests. In particular, they have high activity against arthropods.

Formula (I) provides a general definition of the 1,3,4-oxadiazolin-2-ones according to the invention.

Preferred substituents or ranges of the radicals listed in the formulae mentioned hereinabove and hereinbelow are given below.

$Ar^1$ preferably represents phenyl which is optionally mono- to pentasubstituted by identical or different substituents from the group consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro and cyano.

$Ar^2$ preferably represents the radical

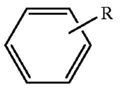

in which

R represents phenyl which is optionally mono- to pentasubstituted by identical or different substituents from the group consisting of CHO, cyano, halogen, $C_1C_{12}$-alkyl, $C_1$–$C_4$-halogenoalkyl, $C_1$–$C_{12}$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio and $C_1$–$C_6$-halogenoalkylthio.

$Ar^1$ particularly preferably represents phenyl which is optionally mono- to trisubstituted by identical or different substituents from the group consisting of fluorine, chlorine, bromine, $C_1$–$C_4$-alkyl, $C_1$–$C_4$-alkoxy, $C_1$–$C_4$-alkylthio; $C_1$–$C_2$-alkyl which is mono- to pentasubstituted by identical or different substituents from the group consisting of fluorine and chlorine, $C_1$–$C_4$-alkoxy which is mono- to pentasubstituted by identical or different substituents from the group consisting of fluorine and chlorine, $SCF_3$, $SCHF_2$, nitro and cyano.

$Ar^2$ particularly preferably represents the radical

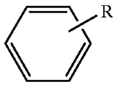

in which

R represents phenyl which is optionally mono- to pentasubstituted by identical or different substituents from the group consisting of CHO, cyano, fluorine, chlorine, bromine, $C_1$–$C_{12}$-alkyl, $C_1$–$C_4$-alkyl which is mono- to hexasubstituted by identical or different substituents from the group consisting of fluorine and chlorine, $C_1$–$C_{12}$-alkoxy, $C_1$–$C_4$-alkoxy which is mono- to hexasubstituted by identical or different substituents from the group consisting of fluorine and chlorine, $C_1$–$C_4$-alkoxy-$C_1$–$C_4$-alkyl, $C_1$–$C_4$-alkoxy-ethyleneoxy, $C_1$–$C_4$-alkylthio and $C_1$–$C_4$-alkylthio which is mono- to hexasubstituted by identical or different substituents from the group consisting of fluorine and chlorine.

$Ar^1$ very particularly preferably represents phenyl which is mono- to trisubstituted by identical or different substituents from the group consisting of fluorine and chlorine.

$Ar^2$ very particularly preferably represents the radical

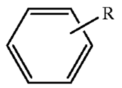

in which

R represents phenyl which is optionally mono- to pentasubstituted by identical or different substituents from the group consisting of CHO, cyano, fluorine, chlorine, bromine, $C_1$–$C_{12}$-alkyl, $C_1$–$C_4$-alkyl which is mono- to hexasubstituted by identical or different substituents from the group consisting of fluorine and chlorine, $C_1$–$C_{12}$-alkoxy, $C_1$–$C_4$-alkoxy which is mono- to hexasubstituted by identical or different substituents from the group consisting of fluorine and chlorine, $C_1$–$C_4$-alkoxy-$C_1$–$C_4$-alkyl, $C_1$–$C_4$-alkoxy-ethyleneoxy, $C_1$–$C_4$-alkylthio and $C_1$–$C_4$-alkylthio which is mono- to hexasubstituted by identical or different substituents from the group consisting of fluorine and chlorine.

$Ar^1$ most particularly preferably represents phenyl which is mono- or disubstituted by identical or different substituents from the group consisting of fluorine and chlorine.

$Ar^2$ most particularly preferably represents the radical

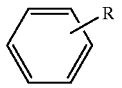

in which

R represents phenyl which is optionally mono- to trisubstituted by identical or different substituents from the group consisting of CHO, cyano, fluorine, chlorine, bromine, $C_1$–$C_8$-alkyl, $C_1$–$C_4$-alkyl which is mono- to hexasubstituted by identical or different substituents from the group consisting of fluorine and chlorine, $C_1$–$C_8$-alkoxy, methoxy or ethoxy, each of which is mono- to pentasubstituted by identical or different substituents from the group consisting of fluorine and chlorine, $C_1$–$C_4$-alkoxy-$C_1$–$C_4$-alkyl, $C_1$–$C_4$-alkylthio, methylthio or ethylthio, each of which is mono- to pentasubstituted by identical or different substituents from the group consisting of fluorine and chlorine.

The abovementioned general or preferred radical definitions or illustrations can be combined with one another as desired, i.e. including combinations across the respective preferred ranges. They apply both to the end products and, correspondingly, to the starting materials and intermediates.

Preference according to the invention is given to those compounds of the formula (I) which contain a combination of the definitions given above as being preferred.

Particular preference according to the invention is given to those compounds of the formula (I) which contain a combination of the definitions given above as being particularly preferred.

Very particular preference according to the invention is given to compounds of the formula (I) which contain a combination of the definitions given above as being very particularly preferred.

Most particular preference according to the invention is given to those compounds of the formula (I) which contain a combination of the definitions given above as being most particularly preferred.

In the radical definitions mentioned hereinabove and hereinbelow, hydrocarbon radicals such as alkyl may be in each case—including in combination with hetero atoms as in alkoxy or alkylthio—straight-chain or branched as far as this is possible.

Preferred compounds according to the invention are substances of the formula (IA):

(IA)

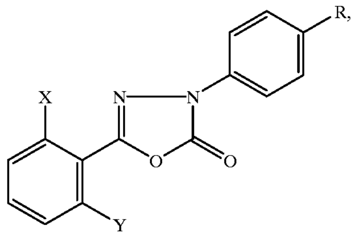

in which

X represents H, F or Cl,

Y represents F or Cl and

R is as defined above.

Examples of the novel compounds according to the invention are listed in Tables 1 to 5.

TABLE 1

Compounds of Table 1 correspond to the general formula (IA) in which

| | | |
|---|---|---|
| X | = | F |
| Y | = | F |
| R | = | as listed below: |

TABLE 2

Compounds of Table 2 correspond to the general formula (IA) in which

| | | |
|---|---|---|
| X | = | H |
| Y | = | F |
| R | = | as listed in Table 1. |

TABLE 3

Compounds of Table 3 correspond to the general formula (IA) in which

| | | |
|---|---|---|
| X | = | H |
| Y | = | Cl |
| R | = | as listed in Table 1. |

TABLE 4

Compounds of Table 4 correspond to the general formula (IA) in which

| | | |
|---|---|---|
| X | = | F |
| Y | = | Cl |
| R | = | as listed in Table 1. |

TABLE 5

Compounds of Table 5 correspond to the general formula (IA) in which

| | | |
|---|---|---|
| X | = | Cl |
| Y | = | Cl |
| R | = | as listed in Table 1. |

Using, for example, N'-[4-(4-trifluoromethoxyphenyl)phenyl]-2,6-difluorobenzoic hydrazide as starting material and trichloromethyl chloroformate as acylating agent, the course of process (a) according to the invention may be illustrated by the following reaction scheme:

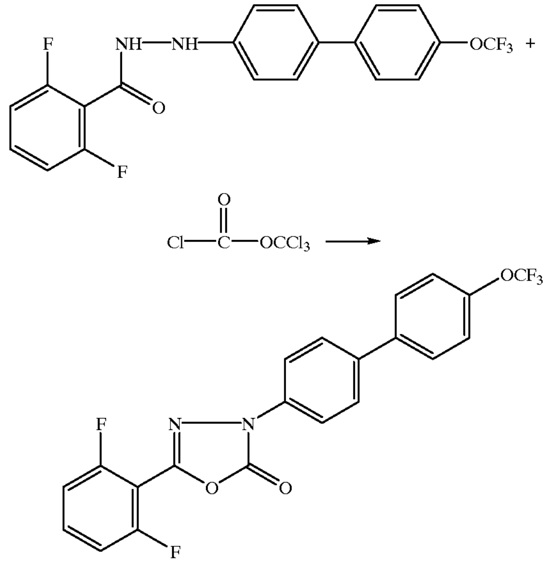

Using, for example, 3-[4-(4-bromophenyl)-phenyl]-5-(2,6-difluorophenyl)-1,3,4-oxadiazolin-2-one and 4-trifluoromethoxyphenylboronic acid as starting materials, the course of process (b) according to the invention may be illustrated by the following reaction scheme:

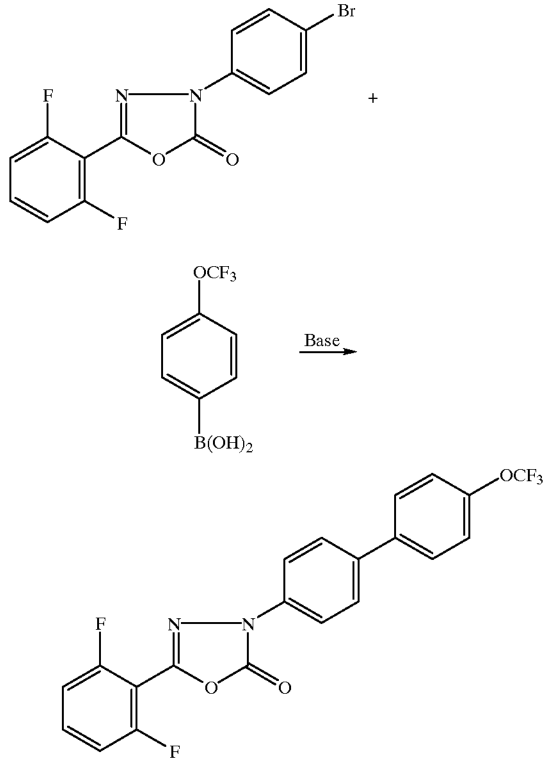

Formula (II) provides a general definition of the hydrazides to be used as starting materials in process (a) according to the invention.

The hydrazides of the formula (II) are known or they can be obtained in a generally known manner (cf. for example U.S. Pat. No. 2,167,793; Revue Roumaine de Chimie 29 (2), 219–22 (1984); Liebigs Annalen der Chemie 1975, 1264). The hydrazides of the formula (II) are obtained for example by reacting activated carboxylic acid derivatives, for example of the formulae (Va–c)

(Va)

$Ar^1$—CO—Cl, (Vb)

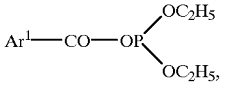

(Vc)

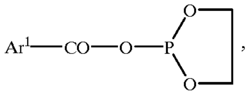

in which $Ar^1$ is as defined above, with hydrazines of the formula (VI)

$Ar^2$—NH—$NH_2$ (VI)

in which $Ar^2$ is as defined above in the presence of a diluent, for example of an optionally halogenated aliphatic or aromatic hydrocarbon such as, for example, methylene chloride or toluene, and, if appropriate, in the presence of a base, for example an organic nitrogen base such as, for example, triethylamine, at temperatures between 0° and 100° C. (cf. also U.S. Pat. No. 2,617,793; Revue Roumaine de Chimie 29 (2), 219–22 (1984));

or by reacting hydrazides of the formula (IIa)

(IIa)

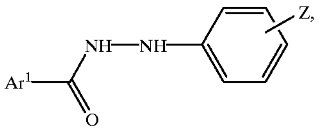

in which $Ar^1$ and Z are each as defined above with boronic acids of the formula (IV) according to process (b) according to the invention (cf. also Comprehensive Organic Synthesis, Vol. III, p. 435–520 (1992) and the Preparation Examples.

The hydrazides of the formula (IIa) are known or obtainable in a simple manner by known methods. They are obtained, for example, by reacting activated carboxylic acid derivatives of the formulae (Va–c) with hydrazines of the formula (VIa)

(VIa)

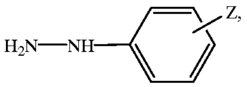

in which

Z is as defined above as described above.

The carboxylic acid derivatives of the formulae (Va–c) and the hydrazines of the formulae (VI) and (VIa) are known and/or can be obtained in a generally known manner.

Furthermore, acylating agents are required as starting materials for process (a) according to the invention. These preferably include chloroformates, in particular trichloromethyl chloroformate, phosgene and methyl chloroformate or ethyl chloroformate.

The acylating agents are generally known compounds of organic chemistry.

Formula (III) provides a general definition of the 3-phenyl-1,3,4-oxadiazolin-2-ones to be used as starting materials for process (b) according to the invention.

Z preferably represents halogen or $—OSO_2CF_3$, particularly preferably bromine or iodine.

Some of the 3-phenyl-1,3,4-oxadiazolin-2-ones of the formula (III) are known (cf. for example EP-A 0 270 061). The 3-phenyl-1,3,4-oxadiazolin-2-ones of the formula (IIIa)

(IIIa)

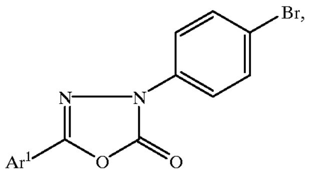

in which $Ar^1$ is as defined above are novel and also form part of the subject matter of the present invention.

The 3-phenyl-1,3,4-oxadiazolin-2-ones of the formula (III), including the novel compounds of the formula (IIIa), can be obtained by process (a) according to the invention.

Formula (IV) provides a general definition of the boronic acids further required as starting materials for carrying out process (b) according to the invention.

The boronic acids of the formula (IV) are generally known compounds of organic chemistry.

Suitable diluents for carrying out processes (a) and (b) according to the invention are all organic solvents which are inert under the reaction conditions in question. If appropriate, they can be used as a mixture with water. Preference is given to using hydrocarbons such as toluene, xylene, tetralene, hexane or cyclohexane, halogenated hydrocarbons such as methylene chloride, chloroform, chlorobenzene or o-dichlorobenzene, ethers such as diethyl ether, diisopropyl ether, dimethoxyethane, tetrahydrofuran or dioxane, nitrites such as acetonitrile or butyronitrile, amides such as dimethylformamide, and furthermore sulfolane.

Suitable bases for carrying out processes (a) and (b) according to the invention are all customary acid acceptors. Preference is given to using tertiary amines such as triethylamine, pyridine, diazabicyclooctane (DABCO), diazabicycloundecene (DBU), diazabicyclononene (DBN), N,N-dimethylaniline, furthermore alkaline earth metal oxides such as magnesium oxide or calcium oxide, and also alkali metal carbonates or alkaline earth metal carbonates such as sodium carbonate, potassium carbonate or calcium carbonate, alkali hydroxides such as sodium hydroxide or potassium hydroxide, furthermore alkoxides such as sodium ethoxide or potassium tert-butoxide.

Suitable catalysts for carrying out process (b) according to the invention are palladium or its compounds or complexes, preferably palladium or tetrakis-(triphenylphosphine)-palladium.

In the practice of processes (a) and (b) according to the invention, the reaction temperatures can be varied over a relatively wide range. In general, the reaction is carried out at temperatures between 0° C. and 150° C., preferably between 0° C. and 100° C., or at the boiling point of the solvent used.

In the practice of process (a) according to the invention, 1 to 5 mol, preferably 1 to 2.5 mol, of acetylating agent and, if appropriate, 1 to 5 mol, preferably 1 to 2.5 mol, of base are employed per mole of hydrazide of the formula (II).

It is also possible to carry out the reaction as a two-step process, i.e. by first adding the acylating agent and subsequent cyclization by heating (cf. also EP-A 0 270 061).

In the practice of process (b) according to the invention, equimolar amounts are generally employed and, if appropriate, 0.01 to 0.1 mol of catalyst and 1 to 5 mol of base are used.

Work-up and isolation of the end products is carried out in the conventional manner.

The active compounds are suitable for controlling animal pests, in particular insects, arachnids and nematodes, encountered in agriculture, in forests, in the protection of stored products and of materials, and in the hygiene sector, and have good plant tolerance and low toxicity to warm-blooded animals. They may advantageously be used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorumi, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp.

The active compounds of the formula (I) according to the invention in particular have outstanding acaricidal activity.

They can be employed particularly successfully, for controlling plant-damaging mites, for example against the red spider mite (*Tetranychus urticae).*

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very finely encapsulated in polymeric substances.

These formulations are produced in a known manner, for example by mixing the active compounds with extenders, that is liquid solvents and/or solid carriers, if appropriate with the use of surfactants, that is emulsifiers and/or dispersants and/or foamers.

If water is used as extender, organic solvents can, for example, also be used as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices such as gum arabic, polyvinyl alcohol and polyvinyl acetate, and natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms prepared from these formulations as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:

2-aminobutane; 2-anilino-4-methyl-6-cyclopropyl-pyrimidine; 2',6'-dibromo-2-methyl-4'-trifluoromethoxy- 4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis,* bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrun, pyridaben, pyrimidifen, pyriproxyfen, quinalphos,

RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active ingredients, such as herbicides, or with fertilizers and growth-regulators is also possible.

The active compounds according to the invention can furthermore be present in their commercially available formulations and in the use forms prepared from these formulations as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

Furthermore, it has been found that the compounds of the formula (I) according to the invention have a potent insecticidal action against insects which destroy industrial materials.

The following insects may be mentioned by way of preferred examples but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec. and *Dinoderus minutus.*

Dermapterans, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be protected against attack by insects are very particularly preferably wood and timber products.

Wood and timber products which can be protected by the composition according to the invention or mixtures comprising such a composition are to be understood as including, for example: construction timber, wooden beams, railway sleepers, bridge components, jetties, wooden vehicles, boxes, pallets, containers, telephone poles, wood lagging, windows and doors made of wood, plywood, particle board, joiner's articles and wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable oils and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers such as, for example, polyvinyl methyl ether, or ketones such as benzophenone or ethylenebenzophenone.

Also particularly suitable as solvent or diluent is water, if appropriate as a mixture with one or more of the above-mentioned organochemical solvents or diluents, emulsifiers and dispersants.

Particularly effective protection of wood is achieved by industrial impregnation processes, for example the vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

EXAMPLE 1

(I-1)

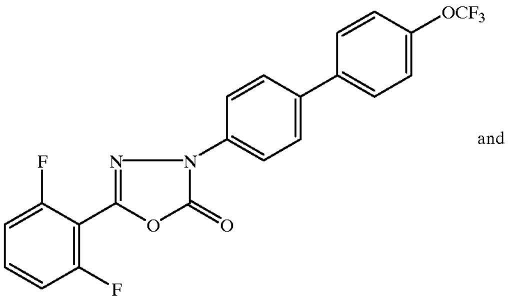

and (III-1)

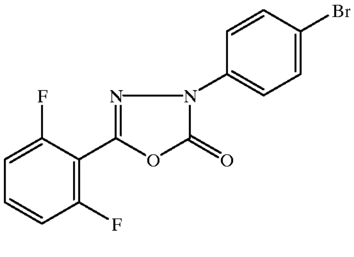

0.7 g (1.7 mmol) of crude (cf. Preparation of the starting material) N'-[4-(4-trifluoromethoxyphenyl)phenyl]-2,6-difluorobenzoic hydrazide are stirred with 0.67 g (3.4 mmol) of trichloromethyl chloroformate in 2 ml of toluene for 0.5 hours at room temperature and then overnight at 65° C. (bath temperature). The reaction mixture is added to a buffer (pH=7) and extracted with ether. The organic phase is dried over sodium sulphate, evaporated and separated by HPLC. 128 mg of 5-(2,6-difluorophenyl)-3-[4-(4-trifluoromethoxyphenyl)phenyl]-1,3,4-oxadiazolin-2-one (I-1)

$^1$H NMR (ppm, in $CDCl_3$): 7.10 (t, 2H); 7.31 (d, 2H); 7.55 (dt, 1H); 7.62 (d, 2H); 7.67 (d, 2H); 8.03 (d, 2H), and 225 mg of 3-(4-bromophenyl)-5-(2,6-difluorophenyl)-1,3,4-oxadiazolin-2-one (III-1) $^1$H NMR (ppm, in $CDCl_3$): 7.10 (t, 2H); 7.54 (dt, 1H); 7.59 (d, 2H); 7.85 (d, 2H).

PREPARATION OF THE STARTING MATERIAL

EXAMPLE (II-1)

(II-1)

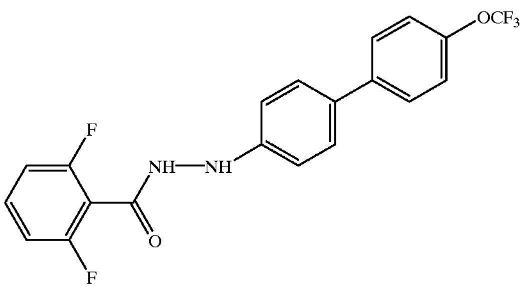

0.65 g (2 mmol) of N'-(4-bromophenyl)-2,6-difluorobenzoic hydrazide and 0.48 g of 4-trifluoromethoxyboronic acid (moist with water) are stirred at 100° C. with 0.62 g of potassium carbonate and a spatula tipful of tetrakis(triphenylphosphine)-palladium in 5 ml of a solvent mixture (water/toluene/ethanol=1:1:0.5) overnight. For work-up, the mixture is poured into water and extracted with ethyl acetate. The organic phase is washed with saturated NaCl solution until neutral, dried over sodium sulphate and then evaporated.

0.9 g of N'-[4-(4-trifluoromethoxyphenyl)phenyl]-2,6-difluorobenzoic hydrazide, which is directly used as crude product for further reactions, is obtained.

EXAMPLE (IIa-1)

(IIa-1)

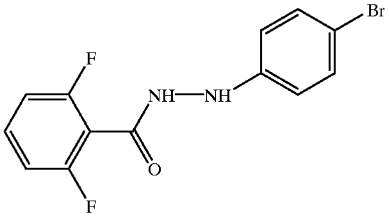

23.3 g (0.10 mol) of 4-bromophenylhydrazine hydrochloride and 20.5 g (0.2 mol) of triethylamine are initially charged in 350 ml of chloroform. At 10° C., 17.6 g (0.1 mol) of 2,6-difluorobenzoyl chloride are then added dropwise and the mixture is stirred at room temperature overnight. For work-up, the mixture is washed once with 10% strength aqueous sodium hydroxide solution, once with dilute hydrochloric acid and once with water. The organic phase is dried over sodium sulphate and then evaporated.

14.7 g (45% of theory) of N'-(4-bromophenyl)-2,6-difluorobenzoic hydrazide of melting point 172° C. are obtained.

By the method of Example 1 and according to the general preparation procedures, the following compounds of the formula (I) are obtained:

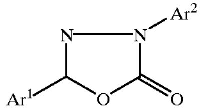

(I)

| Ex. No. | Ar | $Ar^2$ | Mp (° C.) |
|---|---|---|---|
| I-2 | 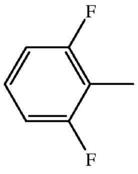 | 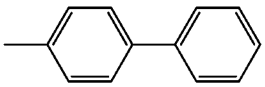 | 129–33 |
| I-3 | 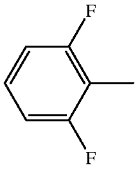 | 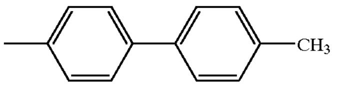 | 147–49 |
| I-4 | 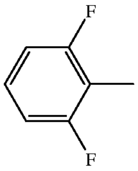 | 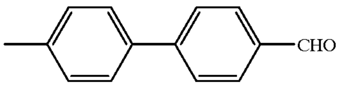 | 172–76 |
| I-5 | 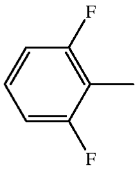 | 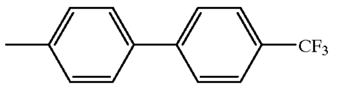 | 132–36 |

USE EXAMPLES

EXAMPLE A

Tetranychus Test (OP resistant/dip treatment)

Solvent: 7 parts by weight of dimethylformamide

Emulsifier: 1 part by weight of alkylaryl polyglycol ether

To produce a suitable active compound preparation, 1 part by weight of active compound is mixed with the stated amount of solvent and the stated amount of emulsifier, and the concentrate is diluted with emulsifier-containing water to the desired concentration.

Bean plants (*Phaseolus vulgaris*) which are heavily infested with all stages of the greenhouse red spider mite *Tetranychus urticae* are dipped into an active compound preparation of the desired concentration.

After the desired period of time, the efficacy in % is determined. 100% means that all the spider mites have been killed; 0% means that none of the spider mites has been killed.

In this test, for example the compound (I-1) of Preparation Example 1 caused a mortality of 98% after 13 days at an exemplary active compound concentration of 0.1%.

We claim:

1. A compound of the formula (I)

(I)

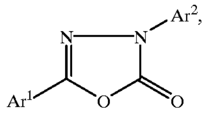

in which $Ar^1$ represents unsubstituted or substituted phenyl and $Ar^2$ represents unsubstituted or substituted biphenyl.

2. A compound of the formula (I) according to claim 1, in which $Ar^1$ represents phenyl which is unsubstituted or mono- to pentasubstituted by identical or different substituents selected from the group consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro and cyano and $Ar^2$ represents the radical

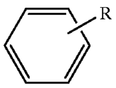

in which

R represents phenyl which is unsubstituted or mono- to pentasubstituted by identical or different substituents selected from the group consisting of CHO, cyano, halogen, $C_1$–$C_{12}$-alkyl, $C_1$–$C_4$-halogenoalkyl, $C_1$–$C_{12}$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio and $C_1$–$C_6$-halogenoalkylthio.

3. A compound of the formula (I) according to claim 1 in which $Ar^1$ represents phenyl which is unsubstituted or mono- to trisubstituted by identical or different substituents selected from the group consisting of fluorine, chlorine, bromine, $C_1$–$C_4$-alkyl, $C_1$–$C_4$-alkoxy, $C_1$–$C_4$-alkylthio; $C_1$–$C_2$-alkyl which is mono- to pentasubstituted by identical or different substituents selected from the group consisting of fluorine and chlorine, $C_1$–$C_4$-alkoxy which is mono- to pentasubstituted by identical or different substituents selected from the group consisting of fluorine and chlorine, $SCF_3$, $SCHF_2$, nitro and cyano and $Ar^2$ represents the radical

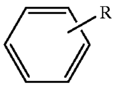

in which

R represents phenyl which is unsubstituted or mono- to pentasubstituted by identical or different substituents selected from the group consisting of CHO, cyano, fluorine, chlorine, bromine, $C_1$–$C_{12}$-alkyl, $C_1$–$C_4$-alkyl which is mono- to hexasubstituted by identical or different substituents selected from the group consisting of fluorine and chlorine, $C_1$–$C_{12}$-alkoxy, $C_1$–$C_4$-alkoxy which is mono- to hexasubstituted by identical or different substituents selected from the group consisting of fluorine and chlorine, $C_1$–$C_4$-alkoxy-$C_1$–$C_4$-alkyl, $C_1$–$C_4$-alkoxy-ethyleneoxy, $C_1$–$C_4$-alkylthio and $C_1$–$C_4$-alkylthio which is mono- to hexasubstituted by identical or different substituents selected from the group consisting of fluorine and chlorine.

4. A compound of the formula (I) according to claim 1, in which $Ar^1$ represents phenyl which is mono- to trisubstituted by identical or different substituents selected from the group consisting of fluorine and chlorine and $Ar^2$ represents the radical

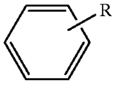

in which

R represents phenyl which is optionally mon- to pentasubstituted by identical or different substituents selected from the group consisting of CHO, cyano, fluorine, chlorine, bromine, $C_1$–$C_{12}$-alkyl, $C_1$–$C_4$-alkyl which is mono- to hexasubstituted by identical or different substituents selected from the group consisting of fluorine and chlorine, $C_1$–$C_{12}$-alkoxy, $C_1$–$C_4$-alkoxy which is mono- to hexasubstituted by identical or different substituents selected from the group cinsisting of fluorine and chlorine, $C_1$–$C_4$-alkoxy-$C_1$–$C_4$-alkyl, $C_1$–$C_4$-alkoxy-ethyleneoxy, $C_1$–$C_4$-alkythio and $C_1$–$C_4$-alkylthio which is mono- to hexasubstituted by identical or different substituents selected from the group consisting of fluorine and chlorine.

5. A compound of the formula (I) according to claim 1 in which $Ar^1$ represents phenyl which is mono- or disubstituted by identical or different substituents selected from the group consisting of fluorine and chlorine and $Ar^2$ represents the radical

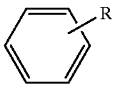

in which

R represents phenyl which is unsubstituted or mono- to trisubstituted by identical or different substituents selected from the group consisting of CHO, cyano, fluorine, chlorine, bromine, $C_1$–$C_8$-alkyl, $C_1$–$C_4$-alkyl which is mono- to hexasubstituted by identical or different substituents selected from the group consisting of fluorine and chlorine, $C_1$–$C_8$-alkoxy, methoxy or ethoxy, each of which is mono- to pentasubstituted by identical or different substituents selected from the group consisting of fluorine and chlorine, $C_1$–$C_4$-alkoxy-$C_1$–$C_4$-alkyl, $C_1$–$C_4$-alkylthio, methylthio or ethylthio, each of which is mono- to pentasubstituted by identical or different substituents selected from the group consisting of fluorine and chlorine.

6. A process for preparing a compound of the formula (I) according to claim 1, comprising reacting a) hydrazides of the formula (II)

(II)

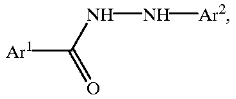

in which $Ar^1$ and $Ar^2$ are each as defined in claim 1 with an acylating agent in the presence of a diluent and in the absence of or in the presence of a base, or reacting b) 3-phenyl-1,3,4-oxadiazolin-2-ones of the formula (III)

(III)

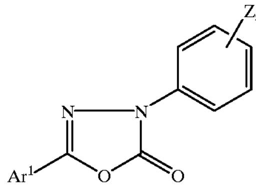

in which $Ar^1$ is as defined above and

Z represents a leaving group with boronic acids of the formula (IV)

$$R—B(OH)_2 \quad (IV),$$

in which

R represents unsubstituted or substituted phenyl in the presence of a base in the absence of or in the presence of a catalyst and in the presence of a diluent.

7. A compound of the formula (IIa)

(IIIa)

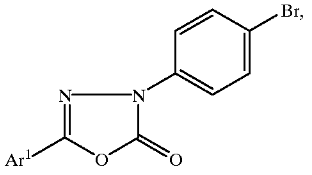

in which $Ar^1$ is as defined in claim 1.

8. A pesticidal composition comprising a pesticidally effective amount of a compound according to claim 1 and an extender.

9. A method of combating unwanted pests which comprises administering to such pests or to a locus from which it is desired to exclude such pests a pesticidally effective amount of a compound according to claim 1.

* * * * *